(12) United States Patent
Kopperschmidt et al.

(10) Patent No.: US 8,460,552 B2
(45) Date of Patent: Jun. 11, 2013

(54) METHOD AND DEVICE FOR THE DETECTION OF DISRUPTIONS OF THE BLOOD FLOW IN AN EXTRACORPOREAL BLOOD CIRCUIT

(75) Inventors: Pascal Kopperschmidt, Dittelbrunn (DE); Malte Gross, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1559 days.

(21) Appl. No.: 10/580,869

(22) PCT Filed: Sep. 11, 2004

(86) PCT No.: PCT/EP2004/010180
§ 371 (c)(1),
(2), (4) Date: Jul. 23, 2008

(87) PCT Pub. No.: WO2005/058390
PCT Pub. Date: Jun. 30, 2005

(65) Prior Publication Data
US 2007/0108128 A1 May 17, 2007

(30) Foreign Application Priority Data
Nov. 25, 2003 (DE) .................. 103 55 042

(51) Int. Cl.
*B01D 11/00* (2006.01)
*B01D 35/00* (2006.01)

(52) U.S. Cl.
USPC ............. 210/645; 210/646; 210/649; 210/87; 210/90

(58) Field of Classification Search
USPC ............................................ 210/645; 73/592
See application file for complete search history.

(56) References Cited

U.S. PATENT DOCUMENTS
2002/0174721 A1* 11/2002 Gross .............................. 73/592

FOREIGN PATENT DOCUMENTS
| DE | 10213179 C1 * | 8/2003 |
| EP | 0 330 761 | 9/1989 |
| EP | 1 245 242 | 10/2002 |
| EP | 1348458 A1 * | 10/2003 |

OTHER PUBLICATIONS
International Search Report, PCT/EP2004/010180, mailed Jan. 18, 2005.

* cited by examiner

*Primary Examiner* — Vickie Kim
*Assistant Examiner* — Allison M Gionta
(74) *Attorney, Agent, or Firm* — Kenyon & Kenyon LLP

(57) ABSTRACT

A method and device that identify impairments of the blood flow in an extra-corporeal blood circuit during extracorporeal treatment of the blood using an extracorporeal haemodialysis device, where the phase angle of at least one harmonic oscillation of an oscillating pressure signal that propagates in the extracorporeal blood circuit is determined. Impairments of the blood flow are detected in the extracorporeal blood circuit based on a characteristic modification of the phase angle of at least one harmonic oscillation of the pressure signal. A temporal modification of the phase angle may be compared with a predefined threshold value and an impairment is detected if the value of the modification of the phase angle is greater than the predefined threshold value. The method and device permit an early identification of a coagulation of the blood that flows through the haemodialysis unit, so that countermeasures can be initiated promptly.

20 Claims, 3 Drawing Sheets

METHOD AND DEVICE FOR THE DETECTION OF DISRUPTIONS OF THE BLOOD FLOW IN AN EXTRACORPOREAL BLOOD CIRCUIT

FIELD OF THE INVENTION

The invention relates to a method and a device for the detection of disruptions of the blood flow in an extracorporeal blood circuit during an extracorporeal blood treatment with an extracorporeal treatment apparatus.

BACKGROUND OF THE INVENTION

For the purpose of removing substances usually eliminated with urine and for the purpose of withdrawing fluid, use is made of various methods for machine-aided blood treatment in acute or chronic kidney failure. In the case of haemodialysis (HD), a patient's blood is conveyed in an extracorporeal blood circuit through one chamber of a dialyser divided by a semipermeable membrane into two chambers, while a dialysing fluid flows through the other chamber. Both a convective and a diffusive substance exchange takes place via the membrane of the dialyser. Only a convective substance exchange is present in the case of haemofiltration (HF). Haemodiafiltration (HDF) is a combination of the two methods.

Known apparatuses for haemodiafiltration have one or more substitution pumps with which physiological fluid is fed to the patient's blood, while fluid is withdrawn via the dialyser or filter of the haemodiafiltration apparatus. The physiological fluid can be fed upstream or downstream of the dialyser to the arterial or venous branch of the extracorporeal circuit. The substitution of the fluid before entry of the blood into the dialyser or filter is referred to as pre-dilution and the substitution after exit of the blood from the dialyser or filter is referred to as post-dilution.

It has been shown that an HDF blood treatment in which a post-dilution takes place has a greater efficiency, with the same substitution delivery quantity, than a treatment in which a pre-dilution takes place. The greater cleaning capacity with the post-dilutive addition of substitution fluid compared with the pre-dilutive substitution can be traced back to the fact that the filtrate is obtained completely from the blood to be cleaned in the case of post-dilution, whereas in the case of pre-dilution the blood diluted with substitution fluid flows into the dialyser or filter before urea toxicants can be taken up during the flow through the patient.

A drawback with pre-dilution lies in the fact that an excessively high ultrafiltration rate, i.e. an excessively great withdrawal of fluid via the membrane of the dialyser or filter, leads to a thickening of the blood and an increase in the flow resistance in the dialyser or filter.

It has been shown that, with raised flow resistance, blood treatment apparatuses are no longer in a position to convey the blood to be cleaned at the set delivery rate, as a result of which the effectiveness of the blood treatment is reduced. The flow resistance in the dialyser or filter can, however, also lead to complete blocking-up of the membrane. The treatment is then interrupted, whereby the whole blood hose system possibly has to be replaced.

The flow resistance in the dialyser or filter on the blood side is dependent on the hematocrit of the blood, the properties of the membrane of the dialyser or filter and the ratio of the delivery quantities from blood pump and substitution pump. An increase in the flow resistance leads to an increase in pressure between the blood pump arranged upstream of the dialyser or filter and the dialyser or filter. Since both the hematocrit of the blood and the membrane properties change in the course of the treatment, a substitution adapted to the conditions is sought in order to increase the efficiency of the treatment.

Existing controls for the substituate delivery are based on a fixed ratio of the delivery rates of the blood pump and the substituate pump. There is known from European patent document EP 1 175 917 A1 a haemodialysis apparatus, wherein the control of two substituate pumps in pre- and/or post-dilute substitution takes place on the basis of the change in the transmembrane pressure or the hematocrit. In order to determine the transmembrane pressure, European patent document EP 1 175 917 A1 proposes that the pressure be measured both in the extracorporeal circuit and also in the dialysing fluid system.

German patent document DE 38 06 248 A1 describes a protective system for monitoring the pressure of the fluid circuit of a medical apparatus, wherein not only the static pressure, but also pressure fluctuations present in the fluid circuit are evaluated. German patent document DE 38 06 248 A1 proposes picking up the phase shift of pressure pulses, which are detected with a pressure sensor, in order to detect interruptions of the flow in the fluid circuit.

A method is known from U.S. Patent Application No. 2002/0174721 A1 for the detection of stenoses in a hose line system during an extracorporeal blood treatment. In order to detect a stenosis, the frequency spectrum of an oscillating pressure signal propagated in the extracorporeal blood circuit is analysed. It is concluded that there is a stenosis when the attenuation of at least one harmonic of the oscillating pressure signal changes.

SUMMARY OF THE INVENTION

An object of the invention is to provide a reliably operating method, which permits the detection of disruptions of the blood flow in an extracorporeal blood circuit, including an increase in the flow resistance up to the possible blocking-up of the membrane of the dialyser or filter. In particularly, the object is to provide a method with which the early detection of disruptions of the blood flow becomes possible.

Another object of the invention is to make available a reliably operating device which enables early detection of disruptions of the blood flow in an extracorporeal blood circuit.

The method and device according to the invention are based on the analysis of an oscillating pressure signal propagated in an extracorporeal blood circuit. With the method and the device, it is not the fundamental component of the oscillating pressure signal, but at least one of the harmonic components of the pressure signal that is analysed. The analysis of the phase angle of at least one harmonic of the pressure signal permits the detection of an impending thickening of the blood, so that countermeasures can be taken in good time. It is concluded that there is a disruption of the blood flow when the phase angle of at least one harmonic experiences a characteristic change. In principle, it is possible to conclude that there is a disruption of the blood flow when a characteristic change of the phase angle of only one harmonic is present. In order to increase the reliability, however, the phase angles of a number of harmonics can also be analysed, whereby the evaluation can take place with the known statistical methods.

An advantage of the method and the device according to the invention lies in the fact that the oscillating pressure signal needs to be measured at only one point of the extracorporeal blood circuit. A relatively straightforward structure of the apparatus results therefrom. The pressure in the venous branch of the extracorporeal circuit is preferably measured downstream of the blood treatment unit, i.e. after fluid has been withdrawn from the blood. The measurement can take place with a venous pressure sensor, which is in any case present in the known blood treatment apparatuses. In principle, the pressure measurement is also possible in the blood treatment unit, for example in the filter cap or the hollow fibres of the dialyser, whereby a change in the phase angle can in principle also be detected upstream of the blood treatment unit on the basis of reflections. This will, however, be refrained from in practice.

The method and the device according to the invention render further measuring cells, e.g. for the determination of the transmembrane pressure or the hematocrit, unnecessary. Additional hardware or software for determining the filter coefficients, for example, is also unnecessary. Furthermore, the blood hose system of the blood treatment apparatus can remain unchanged.

Instead of a differential approach, a critical absolute or relative change in the absolute value of the phase compared to a limiting value can be evaluated as an alarm criterion.

In order to analyse one or more harmonics of the oscillating pressure signal, the change in the phase angle of at least one harmonic in a preset time unit is preferably compared with a preset limiting value, whereby a disruption is detected if the amount of the change in the phase angle is greater than the preset limiting value. It has been shown in tests that the phase angle of a harmonic suddenly falls relatively rapidly before the occurrence of a sharp increase in the flow resistance. It has been shown that a characteristic change in the phase angle occurs particularly markedly with higher-order harmonics. The greater the ordinal number of the harmonic, the more marked the characteristic change.

In the event of disruptions of the blood flow, intervention is preferably undertaken in the control of the extracorporeal blood treatment apparatus in order that countermeasures can be initiated automatically. In principle, however, it is also possible merely to detect the disruption of the blood flow, so that countermeasures can be taken manually if need be.

The method and the device according to the invention offer particular advantages in haemodialysis and/or haemofiltration. As an intervention into the control of the haemodialysis and/or haemofiltration apparatus, it is possible in the event of a disruption to supply a specific quantity of substitution fluid in a preset time interval to the blood upstream of the dialyser. The effect of this is that the blood does not thicken. Alternatively, however, the ultrafiltration rate can also be reduced in a preset time interval. The effect of this is also that the blood does not thicken. It is however also possible both to increase the delivery rate of the substitution fluid and also to reduce the ultrafiltration rate.

In order to ascertain the phase angle of at least one harmonic, it is advantageous to carry out a Fourier analysis of the oscillating pressure signal. This can take place with the known Fourier analysis devices, which operate according to known algorithms.

The Fourier analysis does not have to take place in the form of a mathematical evaluation based on software. Since the frequencies to be filtered are known through the pump speed, use can also be made of hardware filters such as band-pass or comb filters, which are produced with discrete components. This may be of advantage especially when the available computing capacity is limited and the hardware components are available at low cost and in a space-saving form.

For the method and the device according to the invention, the oscillating pressure signal may be generated in different ways. The pressure pulses of the blood pump, in particular an occluding blood pump, for example a roller pump, may be measured, with which the blood is conveyed in the arterial branch.

The mathematical relationship in respect of the calculation of the angular speed is explained in detail below.

As the measured variable, use is made of pressure $p_{ven}(t)$ oscillating with co-determined on the vein side, which is broken down into a higher spectral harmonic of order n by means of the Fourier analysis, the fast Fourier analysis (FFT) or other suitable filter procedures, e.g., comb filter, band-pass filter, etc.

$$A_n = f_n(\omega, p_{ven}) \qquad [1]$$

$$B_n = f^*_n(\omega, p_{ven}) \qquad [2]$$

For example, f and f*, as a complex conjugated function of f, can have the following form:

$$f_n(\omega, p_{ven}) = \int_{T=\frac{2\pi}{\omega}} p_{ven}(t)\sin(n\omega t)\,dt,\ (n \in N) \qquad [3]$$

$$f^*_n(\omega, p_{ven}) = \int_{T=\frac{2\pi}{\omega}} p_{ven}(t)\cos(n\omega t)\,dt,\ (n \in N). \qquad [4]$$

The real coefficients $A_n$ and $B_n$ of the breakdown form a complex number $Z_n$ of the form:

$$Z_n = A_n + iB_n\ (n \in N), \qquad [5]$$

whereby $Z_n$ represents a vector of the plane of complex numbers. The amount of the vector and angle $\Phi$ of the vector in polar coordinates can be ascertained according to:

$$\text{Amount } |Z_n| = |A_n + iB_n| = \sqrt{(A_n + iB_n)(A_n - iB_n)} = \sqrt{A_n^2 + B_n^2} \qquad [6]$$
$$(n \in N)$$

$$\text{Phase: } \phi_n = \arctan\frac{A_n}{B_n} \qquad [7]$$
$$(n \in N)$$

The temporal course of the phase ascertained in [7] is observed and evaluated with respect to a critical speed $\omega_{crit}$:

$$\frac{d}{dt}\phi_n - \omega_{crit,n} = \pm\Delta_n \qquad [8]$$

Evaluation $\Delta_n$ is a measure of the change in the blood-side flow behaviour through the dialyser during a dialysis treatment with a pronounced convective substance transport (HDF, HF), in particular with a large order n.

DETAILED DESCRIPTION

In the following exemplary embodiments a method and device in accordance with the invention are explained in greater detail by reference to the figures.

Figure 1:
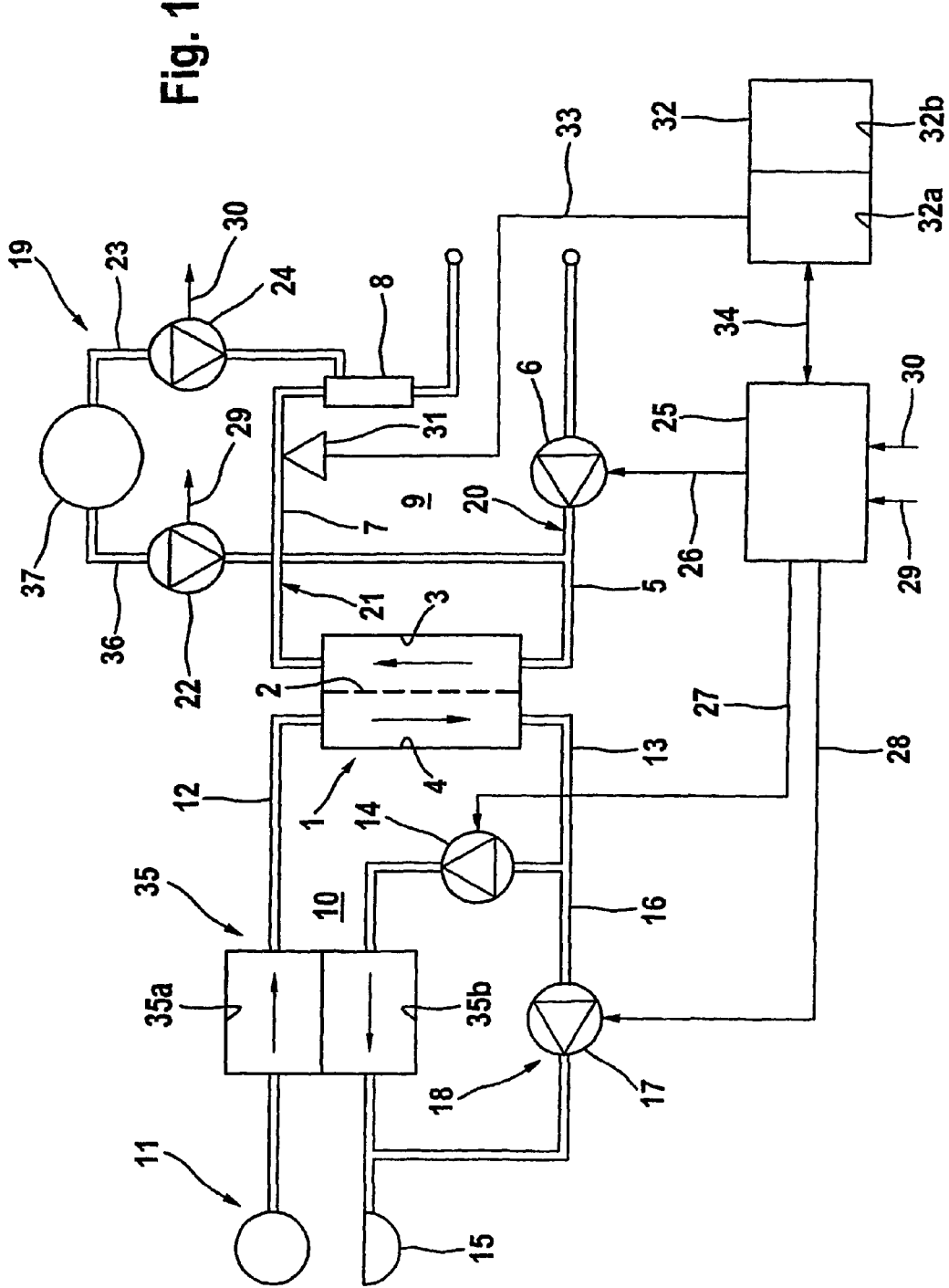
FIG. 1 is a simplified diagrammatic representation of a haemodialysis apparatus together with a device for the detection of disruptions of the blood flow.

FIG. 1 shows the essential components of a haemodialysis apparatus in a simplified diagrammatic representation. The haemodialysis apparatus has a dialyser 1, which is divided by a semipermeable membrane 2 into a blood chamber 3 and a dialysing fluid chamber 4. The inlet of the blood chamber is connected to one end of blood supply line 5, into which a blood pump 6 is incorporated, while the outlet of blood chamber 3 is connected to one end of a blood discharge line 7, into which a drip chamber 8 is incorporated. Blood supply and discharge lines 5, 7 form together with blood chamber 3 of dialyser 1 extracorporeal blood circuit 9 of the dialysis apparatus. Blood supply and discharge lines 5, 7 are hose lines of a hose set inserted into the dialysis apparatus.

Dialysing fluid system 10 of the dialysis apparatus includes a device 11 for the preparation of dialysing fluid, which is connected via the first section of a dialysing fluid supply line 12 to the inlet of first chamber half 35a of a balancing device 35. The second section of dialysing fluid supply line 12 connects the outlet of first balancing chamber half 35a to the inlet of dialysing fluid chamber 4. The outlet of dialysing fluid chamber 4 is connected via the first section of a dialysing fluid discharge line 13 to the inlet of second balancing chamber half 35b. A dialysing fluid pump 14 is incorporated into the first section of dialysing fluid discharge line 13. The outlet of second balancing chamber half 35b is connected via the second section of dialysing fluid discharge line 13 to a drain 15. Branching off from dialysing fluid discharge line 13 upstream of dialysing fluid pump 14 is an ultrafiltration line 16, which also leads to drain 15. An ultrafiltration pump 17 is incorporated into ultrafiltration line 16. The balancing device 35, as described with only one balancing chamber, which has two balancing-chamber halves, serves as merely one possible embodiment for the purpose of explanation. Two balancing chambers can also be provided instead of one balancing chamber. Gravimetric weighing means can also be provided instead of a volumetric balancing device.

During the dialysis treatment, the patient's blood flows through blood chamber 3 and the dialysing fluid flows through dialysing fluid chamber 4 of dialyser 1. Balancing device 35 ensures that only as much dialysing fluid can be supplied via dialysing fluid supply line 12 as dialysing fluid can flow away via dialysing fluid discharge line 13. Fluid can be withdrawn from the patient by means of ultrafiltration pump 17. Ultrafiltration pump 17 is thus part of a device for the withdrawal of fluid from the blood, which is referred to as ultrafiltration device 18.

In order to supply fluid to the patient again, the dialysis apparatus has a substitution device 19, with which a substitution fluid (substituate) can be fed to the blood that is flowing through arterial branch 20 (pre-dilution) and/or venous branch 21 (post-dilution) of extra-corporeal blood circuit 9. Substitution device 19 has a device 37 for the preparation of substituate, from which first substituate line 36, into which first substituate pump 22 is incorporated, leads to the section of blood supply line 5 between blood pump 6 and blood chamber 3. A second substituate line 23, into which second substituate pump 24 is incorporated, leads from device 37 for the preparation of substituate to drip chamber 8.

Moreover, the dialysis apparatus has a central control unit 25, which is connected via control lines 26-30 to blood pump 6, dialysing fluid pump 14, ultrafiltration pump 17 and first and second substitution pumps 22, 24.

The device according to the invention for the detection of disruptions of the blood flow is described as a component part of the blood treatment apparatus, since the blood treatment apparatus already has the necessary hardware. The device according to the invention, however, can in principle also form a separate unit.

The device for the detection of disruptions has a venous pressure sensor 31 arranged up-stream of drip chamber 8 in venous branch 21 of extracorporeal circuit 9 and an evaluation unit 32 which receives the output signal of the pressure sensor via a signal line 33. Evaluation unit 32 is connected via a data line 34 to central control unit 25 of the dialysis apparatus. Evaluation unit 32 and control unit 25 exchange between one another the data required for the blood treatment, so that the control unit can undertake an intervention into the machine control when the evaluation unit detects a disruption.

The function of evaluation unit 32 is described in detail below.

Evaluation unit 32 has a Fourier analysis device 32a, which analyses output signal 33 of venous pressure sensor 31. Blood pump 6, e.g. a roller pump, generates oscillating pressure pulses which are propagated via arterial and venous branches 20, 21 of extracorporeal circuit 9. The oscillating pressure pulses are measured with venous pressure sensor 31 and analysed by means of Fourier analysis device 32a of evaluation unit 32.

The oscillating pressure signal has a static component ($\bar{\omega}=0$) and harmonic components. Since the roller pump is a pump with two rollers, the odd harmonics ($1\bar{\omega}, 3\bar{\omega}, 5\bar{\omega}\ldots$) can be neglected. Fourier analysis device 32a breaks down the oscillating pressure signal into a static component and the even harmonics ($2\bar{\omega}, 4\bar{\omega}, 6\bar{\omega}\ldots$), whereby the phase angle of the harmonics is ascertained in each case.

Figure 2:
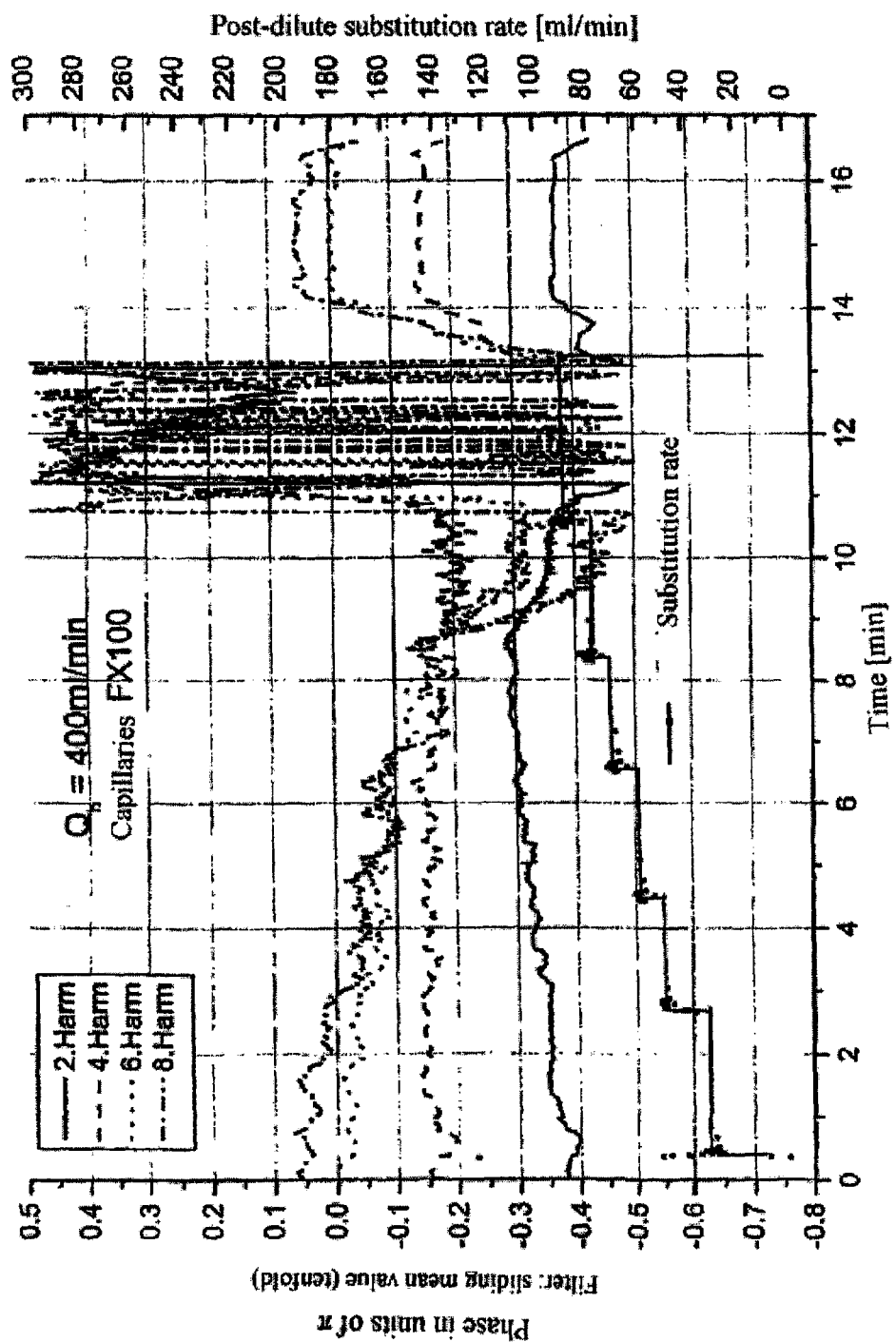
FIG. 2 shows the change in the standardised phase angle, of harmonics of the oscillating pressure signal as a function of the treatment time with a successive increase in the delivery rate of the substitution fluid.

FIG. 2 shows the phase angle of the $2^{nd}$, $4^{th}$, $6^{th}$ and $8^{th}$ harmonic of the oscillating pressure signal as a function of the treatment time in the case of an in-vitro HDF treatment with post-dilution. The substituate delivery rate was successively increased to 90 ml/min, until the pressure in the blood hose segment between the blood pump and the dialyser became unstable. At the same time, the ultrafiltration rate was increased to the same extent. It has been shown that impending thickening of the blood can be detected by a rapid and markedly diminishing phase angle of the individual harmonics. The effect of the post-dilution and the increase in the ultrafiltration rate is that the hollow fibres of the dialyser become blocked up. The increased substitution rate as a consequence of the increase in the ultrafiltration rate, on the other hand, is not the primary influencing magnitude. The phase angle of the harmonics falls sharply at approx. 8-10 minutes. The phase angle in the case of the higher-order harmonics falls particularly sharply. With a further increase in the substitution rate, virtually chaotic fluctuations of the phase angle occur at 10-13 minutes on account of the forming blockage of the membrane of the dialyser.

Apart from Fourier analysis device 32a, evaluation unit 32 has a computing unit 32b for the detection of a characteristic change in the phase angle of individual harmonics. Only the analysis of one harmonic, i.e. the $8^{th}$ harmonic, will be described below. The evaluation can however also take place on the basis of several harmonics.

Computing unit 32b has a differentiator, which differentiates the phase-angle signal. The differential of the phase signal as a function of time is a measure of the decrease in the phase angle. The computing unit compares the differential of the phase-angle signal with a preset limiting value. If the differential exceeds the limiting value, a disruption is assumed. An acoustic and/or optical alarm can be emitted. Since the detection of the disruption takes place before the membrane of the dialyser is blocked up, countermeasures can be taken in good time.

In the case where a disruption is detected, evaluation unit 32 sends a signal via data line 34 to central control unit 25 of the dialysis apparatus in order to initiate an intervention in the machine control. Central control unit 25 controls first substituate pump 22, in such a way that thickening of the blood is counteracted. For this purpose, the delivery rate of substituate pump 22 is increased for a preset time interval in order to supply a specific quantity of substitution fluid upstream of blood chamber 3 of dialyser 1, so that the blood flowing into the dialyser is thinned. Control unit 25 can however also control ultrafiltration device 18 in such a way that the ultrafiltration rate is reduced for a preset time interval, as a result of which thickening of the blood is counteracted. Both countermeasures can however also be initiated at the same time.

As a countermeasure, a control can also be provided such that the return of the phase to an initial value is sought as a target value. This can be achieved in particular by the supply of the post-dilution fluid as pre-dilution fluid. If, for example, a post-dilution takes place at the start, the delivery rate of first substituate pump 22 for pre-dilution can be increased in the event of a change in the phase angle, while the delivery rate of second substituate pump 23 for post-dilution is reduced or kept constant. Depending on the deviation, a counter-control can then take place according to known procedures, for example with a P-controller, PI-controller or PID-controller.

Figure 3:
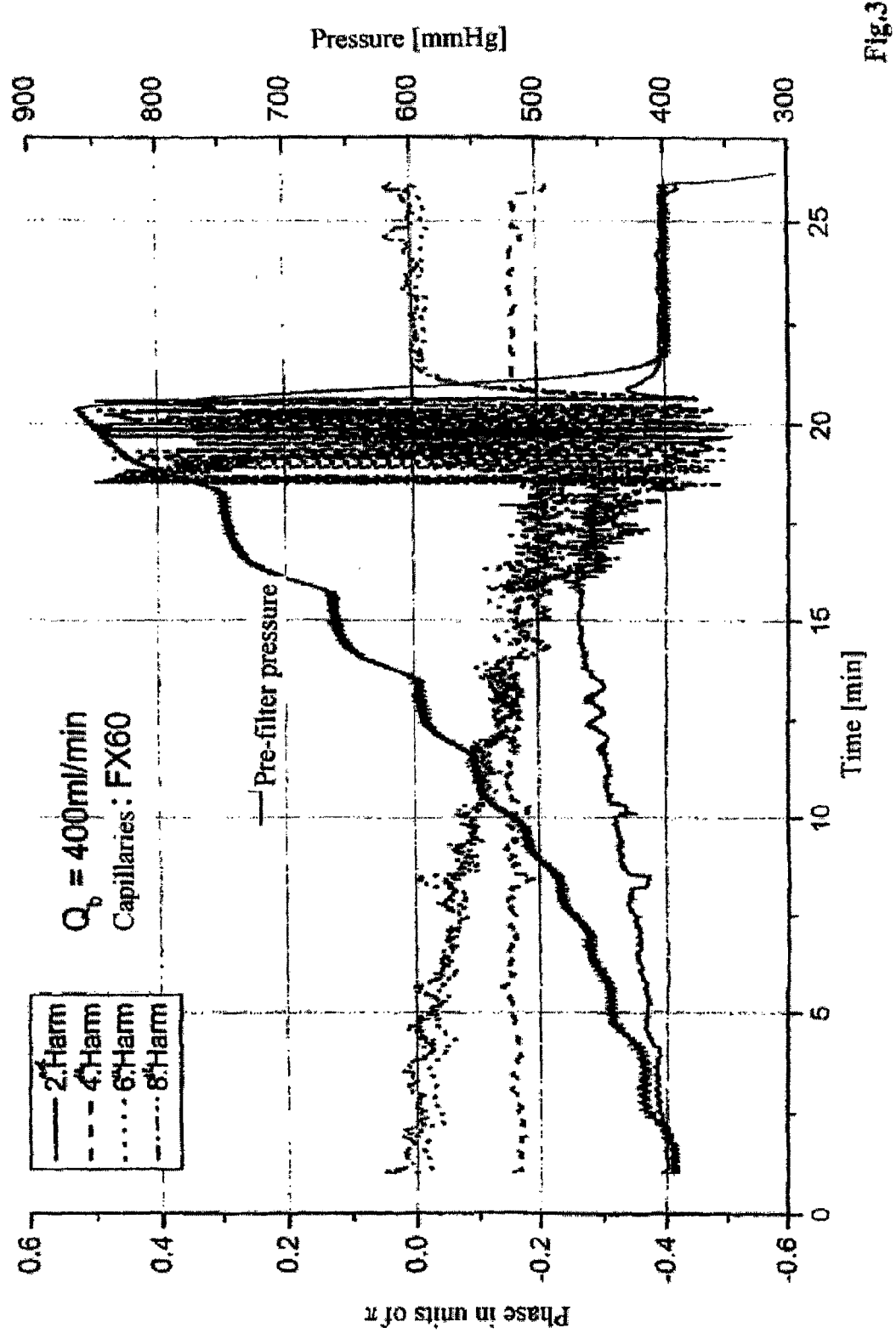
FIG. 3 shows the blood pressure in the arterial branch of the extracorporeal blood circuit as a function of the treatment time with a successive increase in the delivery rate of the substitution fluid.

FIG. 3 shows the arterial pressure in the blood hose segment upstream of blood chamber 3 between blood pump 6 and blood chamber 3 of dialyser 1 (pre-filter pressure) as a function of time with a successive increase of the substitution rate and the ultrafiltration rate and post-dilution. The phases of the $2^{nd}$, $4^{th}$, $6^{th}$ and $8^{th}$ higher harmonics of the oscillating pressure are reproduced at the same time. It can be seen that, after each increase in the substitute rate, a fixed pre-filter pressure is established after a short time in the stable case. If instability occurs as a result of an unfavourable ratio between the delivery quantities of the blood pump and the substitute pump, the pre-filter pressure increases monotonically over time without assuming a constant value. This increase coincides with a drastic increase in the phase angle. The increasing pressure could even lead to a rupture of the dialyser membrane.

The invention claimed is:

1. A method for the detection of disruptions of blood flow in an extracorporeal blood circuit during an extracorporeal blood treatment with an extracorporeal blood treatment apparatus, the extracorporeal blood circuit comprising an arterial branch leading to a blood treatment unit and a venous branch leading away from the blood treatment unit, the method comprising:
   measuring an oscillating pressure signal propagated in the extracorporeal blood circuit; and
   analyzing the oscillating pressure signal, including
   ascertaining the phase angle of at least one harmonic of the oscillating pressure signal and
   detecting a disruption of the blood flow in the extracorporeal blood circuit on the basis of the change in the phase angle of the at least one harmonic.

2. The method of claim 1, further comprising:
   determining a temporal change of the phase angle, wherein the temporal change of the phase angle is determined by ascertaining a change in the phase angle of the at least one harmonic in a preset time unit; and
   comparing the temporal change of the phase angle of the harmonic with a preset limiting value, whereby a disruption is detected if the amount of the change in the phase angle is greater than the preset limiting value.

3. The method of claim 1, further comprising:
   in the event of disruptions of the blood flow, intervening in the control of the extracorporeal blood treatment apparatus.

4. The method of claim 1, wherein the extracorporeal blood treatment apparatus is at least one of a haemodialysis and haemofiltration apparatus and the blood treatment unit is at least one of a dialyser and filter, further comprising:
   withdrawing fluid at a preset ultrafiltration rate from the blood flowing through the extracorporeal blood circuit; and
   feeding substitution fluid to the extracorporeal blood circuit to at least one of an upstream location and a downstream location of the at least one dialyser and filter.

5. The method of claim 4, wherein, in the event of a disruption, a specific quantity of substitution fluid is fed, in a preset time interval, to the blood upstream of at least one of the dialyser and filter as an intervention into the control of at least one of the haemodialysis and haemofiltration apparatus.

6. The method of claim 4, wherein, in the event of a disruption, the ultrafiltration rate is reduced in a preset time interval as an intervention into the control of at least one of the haemodialysis and haemofiltration apparatus.

7. The method of claim 1, wherein a Fourier analysis of the oscillating pressure signal is carried out in order to ascertain the phase angle of the at least one harmonic.

8. The method of claim 1, further comprising: conveying blood in the arterial branch by a blood pump wherein the pressure pulses of the blood pump are measured as the oscillating pressure signal.

9. The method of claim 8, wherein the blood pump is an occluding pump.

10. The method of claim 1, wherein the oscillating pressure signal is measured with a pressure sensor arranged in the venous branch of the extracorporeal blood circuit.

11. A device for the detection of disruptions of blood flow in an extracorporeal blood circuit during an extracorporeal blood treatment with an extracorporeal blood treatment apparatus, the extracorporeal blood circuit comprising an arterial branch leading to a blood treatment unit and a venous branch leading away from the blood treatment unit, the device comprising:
   a means for generating an oscillating pressure signal propagated in the extracorporeal blood circuit;
   a means for measuring the oscillating pressure signal; and
   a means for analyzing the oscillating pressure signal wherein the means for analyzing the oscillating pressure signal includes a means for determining the phase angle of at least one harmonic of the oscillating pressure signal and a means for detecting a change in the phase angle.

12. The device of claim 11, wherein the means for detecting a change in the phase angle is configured such that the change in the phase angle of at least one harmonic is ascertained in a preset time interval and the temporal change in the phase angle of the harmonic is compared with a preset limiting value, whereby a disruption is detected if the amount of the change in the phase angle is greater than the preset limiting value.

13. The device of claim 11, further comprising a means for intervening in the control of the extracorporeal blood treatment apparatus.

14. The device of claim 11, wherein the extracorporeal blood treatment apparatus is at least one of a haemodialysis and haemofiltration apparatus and the blood treatment unit is at least one of a dialyser and a filter, the extracorporeal blood treatment apparatus further comprising:

an ultrafiltration device that withdraws fluid at a preset ultrafiltration rate from the blood flowing through the extracorporeal blood circuit, and a substitution device that supplies substitution fluid to the blood flowing through the extracorporeal blood circuit to at least one of an upstream location and a downstream location of at least one of the dialyser and filter.

15. The device of claim 14, further comprising a means for intervening in the control of at least one of the haemodialysis and haemofiltration apparatus, wherein the means for intervening controls the ultrafiltration device such that, when a disruption is detected, the ultrafiltration rate is reduced in a preset time interval.

16. The device of claim 14, further comprising a means for intervening in the control of at least one of the haemodialysis and haemofiltration apparatus, wherein the means for intervening controls the substitution device such that, when a disruption is detected, a specific quantity of substitution fluid is fed to the blood in a preset time interval upstream of at least one of the dialyser and filter.

17. The device of claim 11, wherein the means for determining the phase angle of at least one harmonic of the oscillating pressure signal includes a Fourier analysis device, which carries out a Fourier analysis of the oscillating pressure signal in order to ascertain the phase angle.

18. The device of claim 11, wherein the means for generating the oscillating pressure signal includes a blood pump arranged in the arterial branch of the extracorporeal blood circuit.

19. The device of claim 18, wherein the blood pump is an occluding pump.

20. The device of claim 11, wherein the means for measuring the oscillating pressure signal includes a pressure sensor arranged in the venous branch of the extracorporeal blood circuit.

* * * * *

UNITED STATES PATENT AND TRADEMARK OFFICE
CERTIFICATE OF CORRECTION

PATENT NO.      : 8,460,552 B2  Page 1 of 1
APPLICATION NO. : 10/580869
DATED           : June 11, 2013
INVENTOR(S)     : Kopperschmidt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2080 days.

Signed and Sealed this
Eighth Day of September, 2015

Michelle K. Lee
*Director of the United States Patent and Trademark Office*